US008052591B2

(12) United States Patent
Mishelevich et al.

(10) Patent No.: US 8,052,591 B2
(45) Date of Patent: Nov. 8, 2011

(54) TRAJECTORY-BASED DEEP-BRAIN STEREOTACTIC TRANSCRANIAL MAGNETIC STIMULATION

(75) Inventors: David J. Mishelevich, Playa del Rey, CA (US); M. Bret Schneider, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 951 days.

(21) Appl. No.: 11/429,504

(22) Filed: May 5, 2006

(65) Prior Publication Data
US 2007/0260107 A1 Nov. 8, 2007

(51) Int. Cl.
*A61N 2/00* (2006.01)
(52) U.S. Cl. ........................................................ 600/14
(58) Field of Classification Search ................. 600/9–15; 607/2, 3
See application file for complete search history.

(56) References Cited

U.S. PATENT DOCUMENTS

| | | | |
|---|---|---|---|
| 4,134,395 A | 1/1979 | Davis | |
| 4,889,526 A | 12/1989 | Rauscher et al. | |
| 5,207,223 A | 5/1993 | Adler | 600/427 |
| 5,267,938 A | 12/1993 | Konotchick | |
| 5,427,097 A | 6/1995 | Depp | 600/427 |
| 5,441,495 A | 8/1995 | Liboff et al. | |
| 5,531,227 A | 7/1996 | Schneider | 128/653.1 |
| 5,707,334 A | 1/1998 | Young | |
| 5,766,124 A | 6/1998 | Polson | |
| 5,891,034 A | 4/1999 | Bucholz | 600/426 |
| 6,042,531 A | 3/2000 | Holcomb | |
| 6,132,361 A | 10/2000 | Epstein et al. | 600/13 |
| 6,132,631 A | 10/2000 | Nallan et al. | 216/16 |
| 6,179,770 B1 | 1/2001 | Mould | |
| 6,179,771 B1 | 1/2001 | Mueller | 600/13 |
| 6,198,958 B1 | 3/2001 | Ives et al. | 600/411 |
| 6,236,875 B1 | 5/2001 | Bucholz et al. | 600/407 |
| 6,266,556 B1 | 7/2001 | Ives et al. | |
| 6,351,573 B1 | 2/2002 | Schneider | 382/294 |
| 6,356,781 B1 | 3/2002 | Lee et al. | |
| 6,425,852 B1 | 7/2002 | Epstein et al. | 600/13 |
| 6,447,440 B1 * | 9/2002 | Markoll | 600/13 |
| 6,461,289 B1 | 10/2002 | Muntermann | 600/9 |
| 6,537,197 B1 | 3/2003 | Ruohonen et al. | |

(Continued)

FOREIGN PATENT DOCUMENTS

DE 10242542 A1 4/2004

(Continued)

OTHER PUBLICATIONS

Agnew et al.; Considerations for safety in the use of extracranial stimulation for motor evoked potentials; Neurosurgery; vol. 20; pp. 143-147; 1987.

(Continued)

*Primary Examiner* — Charles A Marmor, II
*Assistant Examiner* — Christine Hopkins
(74) *Attorney, Agent, or Firm* — Shay Glenn LLP (57) ABSTRACT

The present invention provides for Stereotactic Transcranial Magnetic Stimulation (sTMS) at predetermined locations with the brain or spinal cord and incorporates an array of electromagnets arranged in a specified configuration where selected coils in the array are pulsed simultaneously. Activation of foci demonstrated by functional MRI or other imaging techniques can be used to locate the neural region affected. Imaging techniques can also be utilized to determine the location of the designated targets.

31 Claims, 6 Drawing Sheets

U.S. PATENT DOCUMENTS

| | | | |
|---|---|---|---|
| 6,571,123 B2 | 5/2003 | Ives et al. | 600/544 |
| 6,572,528 B2 | 6/2003 | Rohan et al. | 600/14 |
| 6,663,556 B2 | 12/2003 | Barker | |
| 6,849,040 B2 | 2/2005 | Ruohonen et al. | 600/14 |
| 6,972,097 B2 | 12/2005 | Yoshida et al. | |
| 7,088,210 B2 | 8/2006 | Day et al. | |
| 7,104,947 B2 | 9/2006 | Riehl | |
| 7,153,256 B2 | 12/2006 | Riehl et al. | |
| 7,236,830 B2 | 6/2007 | Gliner | |
| 7,239,910 B2 | 7/2007 | Tanner | |
| 7,320,664 B2 | 1/2008 | Riehl et al. | |
| 7,367,936 B2 | 5/2008 | Myers et al. | |
| 7,396,326 B2 | 7/2008 | Ghiron et al. | |
| 7,483,747 B2 | 1/2009 | Gliner et al. | |
| 2002/0007128 A1 | 1/2002 | Ives et al. | 600/544 |
| 2002/0097125 A1 | 7/2002 | Davey | 336/83 |
| 2003/0004392 A1 | 1/2003 | Tanner et al. | 600/9 |
| 2003/0028072 A1 | 2/2003 | Fischell et al. | |
| 2003/0050527 A1 | 3/2003 | Fox et al. | 600/13 |
| 2003/0065243 A1 | 4/2003 | Tanner | |
| 2003/0204135 A1 | 10/2003 | Bystritsky | 600/407 |
| 2004/0010177 A1 | 1/2004 | Rohan et al. | 600/9 |
| 2004/0077921 A1 | 4/2004 | Becker et al. | 600/9 |
| 2004/0078056 A1 | 4/2004 | Zangen et al. | 607/2 |
| 2004/0193000 A1 | 9/2004 | Riehl | |
| 2004/0193002 A1 | 9/2004 | Tanner et al. | |
| 2004/0204625 A1* | 10/2004 | Riehl et al. | 600/9 |
| 2005/0107655 A1 | 5/2005 | Holzner | |
| 2005/0113630 A1 | 5/2005 | Fox et al. | 600/13 |
| 2005/0148808 A1 | 7/2005 | Cameron et al. | 600/13 |
| 2005/0154426 A1 | 7/2005 | Boveja et al. | |
| 2005/0222625 A1 | 10/2005 | Laniado et al. | 607/2 |
| 2005/0228209 A1 | 10/2005 | Schneider et al. | 600/13 |
| 2005/0234286 A1 | 10/2005 | Riehl et al. | |
| 2006/0058853 A1 | 3/2006 | Bentwich | |
| 2006/0094924 A1 | 5/2006 | Riehl et al. | |
| 2006/0122454 A1 | 6/2006 | Riehl et al. | |
| 2006/0122496 A1 | 6/2006 | George et al. | |
| 2006/0149337 A1 | 7/2006 | John | |
| 2006/0173274 A1 | 8/2006 | George et al. | |
| 2006/0189866 A1 | 8/2006 | Thomas et al. | |
| 2006/0218790 A1 | 10/2006 | Day et al. | |
| 2006/0287566 A1 | 12/2006 | Zangen et al. | |
| 2007/0027353 A1 | 2/2007 | Ghiron et al. | |
| 2007/0027504 A1 | 2/2007 | Barrett et al. | |
| 2007/0100392 A1 | 5/2007 | Maschino et al. | |
| 2007/0265489 A1 | 11/2007 | Fowler et al. | |
| 2009/0024021 A1 | 1/2009 | George et al. | |
| 2009/0187062 A1 | 7/2009 | Saitoh | |

FOREIGN PATENT DOCUMENTS

| | | |
|---|---|---|
| EP | 0501048 A1 | 9/1992 |
| EP | 0709115 A1 | 5/1996 |
| EP | 0788813 A1 | 8/1997 |
| EP | 1326681 B1 | 1/2007 |
| GB | 2271931 A | 5/1994 |
| GB | 2336544 A | 10/1999 |
| WO | WO 98/56302 A1 | 12/1998 |
| WO | WO 99/39769 A1 | 8/1999 |
| WO | WO 99/55421 A2 | 11/1999 |
| WO | WO 00/74777 A1 | 12/2000 |
| WO | WO 00/78267 A2 | 12/2000 |
| WO | WO 02/09811 A1 | 2/2002 |
| WO | WO 02/32504 | 4/2002 |
| WO | WO 03/082405 | 10/2003 |
| WO | WO 2004/087255 A1 | 10/2004 |
| WO | WO 2005/000153 A2 | 1/2005 |
| WO | WO 2006/124914 A2 | 11/2006 |
| WO | WO 2007/050592 A2 | 5/2007 |
| WO | WO 2007/130308 A2 | 11/2007 |

OTHER PUBLICATIONS

Barker, A. T.; An introduction to the basic principles of magnetic nerve stimulation; Journal of Clinical Neurophysiology; vol. 8; No. 1; pp. 26-37; 1991.

Dantec magnetic stimulation product information on MagPro X100 with MagOption; http://www.danica.nl/neuro/neuro-magnetische-stimulatoren.htm; Jan. 15, 2009.

Davey et al.; Designing transcranial magnetic stimulation systems; IEEE Transactions on Magnetics; vol. 41; No. 3; pp. 1142-1148; Mar. 2005.

Epstein et al.; Magnetic coil suppression of visual perception at an extracalcarine site; J. Clin. Neurophysiol; vol. 13; No. 3; pp. 247-252; May 1996.

Lin et al.; Magnetic coil design considerations for functional magnetic stimulation; IEEE Trans. on Biomedical Eng.; vol. 47; No. 5; pp. 600-610; May 2000.

Ruohonen et al.; (Chapter 2); Magnetic stimulation in clinical neurophysiology; Second Ed.; Ed. Elsevier Inc.; pp. 17-30; 2005.

Ueno et al.; Localized stimulation of neural tissues in the brain by means of a paired configuration of time-varying magnetic fields; J. Appl. Phys.; vol. 64; No. 10; pp. 5862-5864; Nov. 15, 1988.

Schneider et al.; U.S. Appl. No. 12/324,227 entitled "Transcranial magnet stimulation of deep brain targets," filed Nov. 26, 2008.

Schneider et al.; U.S. Appl. No. 12/185,544 entitled "Monophasic multi-coil arrays for transcranial magnetic stimulation," filed Aug. 4, 2008.

Mark S. George, "Stimulating the Brain," *Scientific American*, Sep. 2003, pp. 67-73.

Yiftach Roth et al., "A Coil Design for Transcranial Magnetic Stimulation of Deep Brain Regions," *Journal of Clinical Neurophysiology*, (2002), vol. 19, No. 4, pp. 361-370.

Kent R. Davey et al., "Suppressing the Surface Filed During Transcranial Magnetic Stimulation," *IEEE Transactions on Biomedical Engineering*, Feb. 2006, vol. 53, No. 2, pp. 190-194.

Sackheim, H.A., Commentary: Magnetic Stimulation Therapy and ECT, *Convulsive Therapy*, (1994), vol. 10, No. 4, pp. 255-285.

Schneider et al.; U.S. Appl. No. 12/402,404 entitled "Robotic apparatus for targeting and producing deep, focused transcranial magnetic stimulation," filed Mar. 11, 2009.

Nadeem et al.; Computation of electric and magnetic stimulation in human head using the 3-D impedance method; IEEE Trans on Biomedical Eng; vol. 50; No. 7; pp. 900-907; Jul. 2003.

Sekino et al.; Comparison of current distributions in electroconvulsive therapy and transcranial magnetic stimulation; J. of Applied Physics; vol. 91; No. 10; pp. 8730-8732; May 15, 2002.

Avery et al.; A Controlled Study of Repetitive Transcranial Magnetic Stimulation in Medication-Resistant Major Depression; Biological Psychiatry; vol. 59; pp. 187-194; 2005.

Barker et al.; Non invasive magnetic stimulation of the human motor cortex; Lancet; vol. 1; pp. 1106-1110; 1985.

Basser et al.; Stimulation of myelinated nerve axon by electromagnetic induction; Medical & Biological Engineering and Computing.; vol. 29; pp. 261-268; 1991.

Bohning et al.; Mapping transcranial magnetic stimulation (TMS) fields in vivo with MRI; NeuroReport; vol. 8; No. 11; pp. 2535-2538; Jul. 28, 1997.

Conca et al.; Effect of chronic repetitive transcranial magnetic stimulation on regional cerebral blood flow and regional cerebral glucose uptake in drug treatment-resistant depressives. A brief report; Neuropsychobiology; vol. 45; No. 1; pp. 27-31; 2002.

Davey et al.; Modeling the effects of electrical conductivity of the head on the induced electrical field in the brain during magnetic stimulation; Clinical Neurophysiology; vol. 114; pp. 2204-2209; 2004.

Davey et al.; Prediction of magnetically induced electric fields in biologic tissue; IEEE Transactions on Biomedical Engineering; vol. 38; pp. 418-422; 1991.

DeRidder et al.; Transcranial magnetic stimulation for tinnitus: influence of tinnitus duration on stimulation parameter choice and maximal tinnitus suppression; Otol Neurotol.; vol. 26; No. 4; pp. 616-619; Jul. 2005.

Han et al.; Multichannel magnetic stimulation system design considering mutual couplings among the stimulation coils; IEEE Trans. on Biomedical Engineering; vol. 51; No. 5; pp. 812-817; May 2004.

Hovey, C. et al.; The new guide to magnetic stimulation; The Magstim Company Ltd.; Carmarthenshire, United Kingdom; 2003.

Huang et al.; Theta Burst Stimulation of the Human Motor Cortex; Neuron; vol. 45; pp. 201-206; 2005.

Isenberg et al.; Low frequency rTMS stimulation of the right frontal cortex is as effective as high frequency rTMS stimulation of the left frontal cortex for antidepressant-free, treatment-resistant depressed patients; Ann Clin Psychiatry; vol. 17; No. 3; pp. 153-159; Jul.-Sep. 2005.

Lang et al.; How does transcranial DC stimulation of the primary motor cortex alter regional neuronal activity in the human brain?; Eur. J. Neurosci.; vol. 22; No. 2; pp. 495-504; Jul. 2005.

Martin et al.; Transcranial magnetic stimulation for treating depression; Cochrane Review; 2002 (In (eds.): The Cochrane Library. Oxford: Update Software: The Cochrane Library. Oxford: Update Software.).

Ohnishi et al.; rCBF changes elicited by rTMS over DLPFC in humans; Suppl Clin Neurophysiol.; vol. 57: pp. 715-720; 2004.

Ruohonen et al.; Focusing and targeting of magnetic brain stimulation using multiple coils; Medical & Biological Engineering and Computing; vol. 35; pp. 297-301; 1998.

Ruohonen et al.; Theory of Multichannel Magnetic Stimulation: Toward Functional Neuromuscular Rehabilitation; IEEE Transactions on Biomedical Engineering; vol. 46, No. 6; pp. 646-651; Jun. 1999.

Ruohonen, J.; Transcranial magnetic stimulation: modelling and new techniques; (doctoral dissertation); Helsinki Univ. of Tech.; Dept. of Eng. Physics and Mathematics; Espoo, Finland; 1998.

Speer et al.; Opposite effects of high and low frequency rTMS on regional brain activity in depressed patients; Biol. Psychiatry; vol. 48; No. 12; pp. 1133-1141; Dec. 15, 2000.

Takano et al.; Short-term modulation of regional excitability and blood flow in human motor cortex following rapid-rate transcranial magnetic stimulation; Neuroimage; vol. 23; No. 3; pp. 849-859; Nov. 2004.

Traad, Monique; A Quantitative Positioning Device for Transcranial Magnetic Stimulation; Engineering in Medicine and Biology Society; 1990; Proceedings of the 12th Annual Int'l Conf. of the IEEE; Philadelphia, PA; p. 2246; Nov. 1-4, 1990.

Vayssettes-Courchay et al.; Role of the nucleus tractus solitarii and the rostral depressive area in the sympatholytic effect of 8-hydroxy-2-(di-n-propylamino)tetralin in the cat; Eur. J. Pharmacol.; vol. 242; No. 1; pp. 37-45; Sep. 21, 1993.

Wagner et al.; Three-dimensional head model simulation of transcranial magnetic stimulation; IEEE Trans. on Biomedical Engineering; vol. 51; No. 9; pp. 1586-1598; Sep. 2004.

Wasserman et al.; Therapeutic application of repetitive magnetic stimulation: a review; Clinical Neurophysiology; vol. 112; pp. 1367-1377; 2001.

Wasserman, E. M.; Risk and safety of repetitive transcranial magnetic stimulation: report and suggested guidelines from the international Workshop on the Safety of Repetitive Transcranial Magnetic Stimulation, Jun. 5-7, 1996; Electro-encephalography and Clinical Neurophysiology; vol. 108; pp. 1-16; 1998.

Xiao et al.; Magnetic Nanocomposite Paste: An Ideal High-μ, k and Q Nanomaterial for Embedded Inductors in High Frequency Electronic Appls.; Proceedings of the 9th World Multiconference on Systemics, Cybernetics and Informatics; Orlando, FL; Jul. 10-13, 2005.

Partsch et al.; U.S. Appl. No. 12/669,882 entitled "Device and method for treating hypertension via non-invasive neuromodulation," filed Jan. 20, 2010.

Schneider et al.; U.S. Appl. No. 12/671,260 entitled "Gantry and switches for position-based triggering of tms pulses in moving coils," filed Jan. 29, 2010.

Mishelevich et al.; U.S. Appl. No. 12/670,938 entitled "Firing patterns for deep brain transcranial magnetic stimulation," filed Jan. 27, 2010.

Schneider et al.; U.S. Appl. No. 12/701,395 entitled "Control and coordination of transcranial magnetic stimulation electromagnets for modulation of deep brain targets," filed Feb. 5, 2010.

Mishelevich et al.; U.S. Appl. 12/677,220 entitled "Focused magnetic fields," filed Mar. 9, 2010.

Mishelevich et al.; U.S. Appl. No. 12/679,960 entitled "Display of modeled magnetic fields," filed Mar. 25, 2010.

Mishelevich et al.; U.S. Appl. No. 12/680,749 entitled "Intra-session control of transcranial magnetic stimulation," filed Mar. 30, 2010.

Mishelevich et al.; U.S. Appl. No. 12/680,912 "Transcranial magnetic stimulation with protection of magnet-adjacent structures," filed Mar. 31, 2010.

Magstim Website: http://www.magstim.com/magneticstimulators/magstimacc/12494.html (printed Mar. 23, 2010).

Mayberg et al.; Deep brain stimulation for treatment-resistant depression; Neuron; vol. 45; pp. 651-660; 2005.

Schneider et al.; U.S. Appl. No. 12/838,299 entitled "Transcranial magnetic stimulation field shaping," filed Jul. 16, 2010.

Schneider et al.; U.S. Appl. No. 12/912,650 entitled "Sub-motor-threshold stimulation of deep brain targets using transcranial magnetic stimulation," filed Oct. 26, 2010.

Mishelevich et al.; U.S. Appl. No. 12/990,235 entitled "Transcranial magnetic stimulation by enhanced magnetic field perturbations," filed Oct. 29, 2010.

Mishelevich et al.; U.S. Appl. No. 12/917,236 entitled "Treatment of clinical applications with neuromodulation," filed Nov. 1, 2010.

* cited by examiner

TRAJECTORY-BASED DEEP-BRAIN STEREOTACTIC TRANSCRANIAL MAGNETIC STIMULATION

FIELD OF INVENTION

This invention relates to systems for Stereotactic Transcranial Magnetic Stimulation of the brain to modulate neural activity at arbitrary deep and superficial brain locations.

BACKGROUND OF THE INVENTION

Transcranial Magnetic Stimulation (TMS) and Repetitive Transcranial Magnetic Stimulation (rTMS, a variant of TMS in which electromagnetic fields are produced in trains of multiple short pulses) have shown the ability to trigger neuronal firing in selected superficial brain regions. In at least one psychiatric condition (major depression), this effect of TMS and of rTMS appears to constitute an effective therapy. TMS and rTMS instrumentation are currently limited by their inability to focus their magnetic fields at depth. This is chiefly because a magnetic field always diminishes as a function its distance from the source.

Several techniques have been used to deliver stimulation to deep regions of the brain, as will be described. In the use of such technologies, MRI and other imaging techniques are useful for helping to ensure that the stimulation is directed to the correct brain structure. Methods for co-registering internal anatomy with medical instruments, and planning treatment with such medical devices are known in the art, and include methods provided in U.S. Pat. No. 5,207,223 (Adler), U.S. Pat. Nos. 5,891,034 and 6,236,875 (Bucholtz), and by U.S. Pat. Nos. 5,531,227 and 6,351,573 (Schneider). Such registration may be accomplished with the help of commercially available devices designed for surgical navigation, such devices including the Polaris system by Northern Digital (Waterloo, Ontario, Canada).

Magnetic stimulation of the brain and spinal cord has been known since the mid-1980's. Barker A T, Jalinous R, Freeston I L, "Non invasive magnetic stimulation of the human motor cortex" Lancet, 1985; 1:1106-110. A wide variety of clinical applications have been demonstrated, Wassermann, E. M., and S. H. Lisanby, "Therapeutic application of repetitive magnetic stimulation: a review," *Clinical Neurophysiology,* 112:1367-1377, 2001, with the major opportunity appearing to be in depression. Martin J L R, Barbanoj M J, Schlaepfer T E, Clos S P V, Kulisevsky J, A G (2002): Transcranial magnetic stimulation for treating depression (Cochrane Review). In (eds.): The Cochrane Library. Oxford: Update Software: The Cochrane Library. Oxford: Update Software.

Several patents and patent applications relate to such areas as electromagnetic coil design, simultaneous monitoring of EEG, simultaneous monitoring with functional MRI, and specific clinical applications. Among these are U.S. Pat. No. 6,179,771, Mueller, on coil arrangement U.S. Pat. No. 6,198,958, Ives and Pascual-Leone on monitoring of functional MRI during TMS U.S. Patent Application 20020007128 and U.S. Pat. No. 6,571,123, Ives and Pascual-Leone on monitoring of the EEG during TMS U.S. Patent Application 20040078056 and European Patent EP1326681, Zangen et al. on coil design U.S. Patent Application 20020097125, Davey on coil design U.S. Pat. No. 6,132,361, Epstein and Davey, coil design and clinical applications.

Fox P, Lancaster J, Dodd S. Apparatus and Methods for Delivery of Transcranial Magnetic Stimulation. United States Patent Application U.S. 2003/0050527 A1

Fox P, Lancaster J, Apparatus and Methods for Delivery of Transcranial Magnetic Stimulation. United States Patent Application U.S. 2005/0113630 A1

Schneider M B, Mishelevich D J "Robotic Device for Providing Deep, Focused Transcranial Magnetic Stimulation". United States Patent Application U.S. 20050228209 A1.

While stimulation has shown promise in the treatment of depression, the limitation of the rTMS technique to the stimulation of only superficial structures has been a significant restriction. Depression itself has only been treatable because the superficial structures that are stimulated have neural connections to deep structures where the desirable effects actually occur. One way to increase the magnetic field delivered to depth would be increase the power input to the stimulating electromagnet. Unfortunately, simply increasing the output of the electromagnet is prevented from achieving the desired effect because of the proportional increase at the superficial location, where the field is much stronger to begin with. The resultant magnetic field could easily overwhelm the superficial structures and cause pain, unintended activation of non-targeted structures, possibly seizures and neural excitotoxicity.

The general effect of transcranial magnetic stimulation is the depolarization of neural membranes and the resultant production of action potentials. Magnetic fields stimulate neural tissue because electrical current flow is induced. See Davey, K. R., C. H. Cheng, et al. (1991). Prediction of magnetically induced electric fields in biologic tissue. IEEE Transactions on Biomedical Engineering 38: 418-422; Davey, K. R., C. M. Epstein, et al. (2004). Modeling the Effects of Electrical Conductivity of the Head on the Induced Electrical Field in the Brain During Magnetic Stimulation. Clinical Neurophysiology 114: 2204-2209.

When the flow of electrical charges in the intracellular and extracellular compartments is interrupted by a neural membrane, a differential voltage is generated across that membrane. The cell membrane is either depolarized or hyperpolarized depending on the direction of the current flow. That direction of the induced electrical-current flow is determined by the directionality of the magnetic field. The embodiments described herein utilize arrays of magnets arranged such that when the coils are simultaneously energized, individual vector components of the applied magnetic field can be, to a functional extent, spatially segregated. By "spatially segregated" it is meant that the arrangement of coils creates regions of enhanced field strength and regions of diminished field strength in the magnetic field in predetermined spatial locations.

Ruohonen, J., "Transcranial Magnetic Stimulation: Modeling and New Techniques" Ph.D. Dissertation in Engineering, Helsinki University of Technology, Espoo, Finland (52 pages), 1998 has presented a potential theoretical model for neural activation by magnetic fields inducing electrical currents. Five cases are described. Case 1: if the induced electrical field is uniform and parallel to the long axis of the axon, no polarization occurs. Case 2: if the magnetic field induces an electrical current with a gradient, the axon membrane has zones of depolarization and hyperpolarization. Case 3: even in the presence of a uniform field, depolarization will occur at an axon bend. Case 4: transverse activation can produce depolarization and hyperpolarization on opposite sides of the axon. Case 5: depolarization occurs at neural terminations even in the presence of a uniform electrical field. Cases 3 and 5 likely represent the situation with the brain where the axons tend to be thin and curved while Case 4 is representative of the situation in peripheral nerves (e.g., the ulna nerve in the arm) where the nerves tend to be both longer and thicker. TMS is thought to impact axons rather than cell bodies.

There is some evidence that, when applied at rates of approximately one pulse per second or less, recipient nerves are inhibited, or down-regulated in their activity. At rates greater than one pulse per second, the result tends to be excitatory for affected neurons. Stimulating at too great a rate can cause seizures Wassermann, E. M., 1998) "Risk and safety of repetitive transcranial magnetic stimulation: report and suggested guidelines from the International Workshop on the Safety of Repetitive Transcranial Magnetic Stimulation, Jun. 5-7, 1996," Electroencephalography and Clinical Neurophysiology, 108:1-16, 1998.

Because TMS apparatuses are physically large and bulky, and because their use at effective power levels is generally not comfortable, applying continuous stimulation over a period of hours, days or beyond is not practical. Still, a prolonged therapeutic effect of for example, in the case of depression (Martin et al., 2002) and tinnitus De Ridder D, Verstraeten E, Van der Kelen K, De Mulder G, Sunaert S, Verlooy J, Van de Heyning P, Moller A. Transcranial magnetic stimulation for tinnitus: influence of tinnitus duration on stimulation parameter choice and maximal tinnitus suppression. Otol Neurotol. 2005 July;26(4):616-9 most likely occur because of a retraining of pathways and activity levels.

Factors that influence the strength of neural stimulation depend on many factors including:
(a) Coil configuration—The majority of electromagnets used in clinical treatment are double coils, typically each coil having an outer diameter of 70 mm. The radial component of such an electromagnet is the direction that is geometrically normal (perpendicular) to the plane of the coil face;
(b) Coil size;
(c) Coil material;
(d) Pulse strength;
(e) Pulse shape;
(f) Pulse frequency;
(g) The electrical conductive properties and geometry of each specific area of anatomy receiving magnetic pulses; and
(h) The direction of the nerve or nerve tract receiving the generated electrical field in relation to the direction of the magnetic field at that point. (Ruohonen, 1998; Basser P J, Roth B J. Stimulation of myelinated nerve axon by electromagnetic induction. Med Biol Eng Comput. 29, 261-268. 1998; Fox et al. in U.S. Patent Applications 20050113630 and 20030050527).

Small coils (e.g., 20 to 30 mm in diameter) deliver energy with greater focus than their larger counterparts (Ruohonen, J. and R. J. Ilmoniemi, "Focusing and targeting of magnetic brain stimulation using multiple coils," Medical & Biological Engineering and Computing, 35:297-301, 1998; Han, B. Y., Chun, I. K., Lee, S. C., and S. Y. Lee, "Multichannel Magnetic Stimulation System Design Considering Mutual Couplings Among the Stimulation Coils," IEEE Transactions on Biomedical Engineering, 51:812-817, 2004, and Mueller, U.S. Pat. No. 6,179,771). Unfortunately, the smaller the coil, the less field strength it is able to generate at any given level of electrical input. Increasing the current vastly increases the cooling needs of the magnets. Because of the rapid rate of magnetic field strength fall off with distance from the coil, and the difficulty in providing efficient cooling mean, highly focal coils tend to have little ability to penetrate to depth. For a given magnet, for distances that are small relative to the radius of the magnet's coils, the fall off of magnetic field is a property of the magnet itself. For distances that are large relative to the size of the magnet, the fall-off is one over the distance cubed. This factor limits the ability for the magnetic fields of small coils to penetrate to depth. It should be emphasized that for none of the multi-coil arrays described in the cited literature was delivery to depth an objective, nor would they have been capable of that effect, even with adequate power and cooling, given the obtuse angle of their field confluence, their low power, and melting that uncooled coils of that size and configuration would have undergone at high power delivery. In fact, Ruohonen, et al. state that focusing at depth is not possible, reasoning that the discordance between the location of a magnetic field maxima and an electric field maxima may be displaced (an effect that may be compensated for as described by herein by the inventors), and that the magnetic field entering a head has no radial component (an effect of limited significance if true, and also contested by researchers including Wagner, et al, cited below).

The Hesed coil (Zangen et al., U.S. Patent Application 20040078056 and European Patent EP1326681) was developed in order to more efficiently deliver magnetic field to depth. As a result of its design, the fall-off rate for magnetic field strength over distance is less steep than for conventional TMS coils. However this improved depth penetration is achieved with an overall decline in locality when compared with conventional coils. When a magnetic field is applied in the manner described in these references, the intensity of the magnetic field at depth is always less than that at the surface.

The most focal means used today for providing brain stimulation at depth is by use of current-pulsed surgically implanted electrodes, also known as deep-brain stimulation "DBS". Used for the treatment of conditions such as Parkinson's Disease, DBS also hold promise for the treatment of many neurological and psychiatric disorders, due to its ability to selectively activate and inactivate precise regions of the brain. Unfortunately, DBS necessarily involves an invasive neurosurgical procedure, which is expensive, and fraught with medical risks including intracranial bleeding and infection.

It would be desirable to non-invasively achieve the benefits of DBS by directing electromagnetic energy into deep structures without overwhelming superficial structures. It has been proposed in commentary to simultaneously use multiple coils to summate in deep structures (Sackheim H A. Magnetic Stimulation Therapy and ECT (Commentary). Convulsive Therapy 1994; 10(4); 255-8). Work by Bohning and George (Bohning D E, Pecheny A P, Epstein C M, Speer A M, Vincent D J; Dannels W; George M S Mapping transcranial magnetic stimulation (TMS) fields in vivo with MRI. NeuroReport Volume 8(11), 28 Jul. 1997, p 2535-2538) illustrated the reinforcing effect of simultaneously applied magnetic fields. Two pulsed magnetic fields were delivered at an unspecified acute angle from opposite sides of the temples. The resultant magnetic fields were demonstrated to have a reinforcing effect such that the magnetic field demonstrated to be higher at the midline of the brain than it would have had only a single magnet been present. However, this work did not produce or teach a magnetic coil configuration that would enable the intensity at depths to exceed that on the surface, and no further efforts at improving the process were documented.

Fox, et al., (U.S. Patent Applications US 2003/0050527 A1, and U.S. Patent Application US 2005/0113630 A1) propose means for positioning a TMS coil so as to have a maximal biological effect to nerve tissue. This method is based on the use of a single coil targeting a point on the superficial cortex of the brain, and does not discuss the use of multi-coil arrays or concentrating energy at depth.

An alternative approach to non-invasively providing deep brain stimulation using magnetic coils is provided by the inventors of the present invention in Schneider M. B, and D. J. Mishelevich, U.S. Patent Application US 20050228209 A1.

Prior works known by Applicant fall short of configuring coil arrays so as to produce a specific biological effect at a specific locus deep in the brain without significantly impacting superficial structures.

A method for non-invasively modulating the activity of neural tissue at depth at selectable arbitrary locations with the human body, without overwhelming superficial neural structures, would provide significant medical benefits. Additional objects and advantages sought to be achieved by various ones of the methods and systems disclosed herein include:

(a) to provide a system allowing the user to concentrate more magnetic field at depth than at superficial locations that are closer to the stimulating electromagnets, thereby reducing discomfort as well as the risks of seizure and excitotoxicity.
  (b) to provide a system that is both non-invasive and more cost effective than implanted Deep Brain Stimulation with electrodes,
  (c) to provide a method by which the aim of a neuromodulation device such as that described herein may be offset from the target structure in order to compensate for predicted or observed magnetic/electric field discordance.
  (d) to give easy access to a wide variety of neural targets at depth, thereby greatly increasing the breadth of conditions that can be treated such as chronic pain, Alzheimer's Disease, obsessive compulsive disorder, addictions, obesity, Parkinson's Disease and other conditions.
  (e) to provide a more effective treatment of depression, which while it can currently be treated with conventional rTMS, could be treated more effectively by direct impact on targets instead of using indirect pathways as is done with prior art methods.

DETAILED DESCRIPTION

The present application describes a system and method for stereotactic transcranial magnetic stimulation or modulation ("sTMS"). The disclosed system and method uses an array of coils arranged in a predetermined configuration and pulsed substantially simultaneously so that at select spatial vectors, the magnetic field strength at a deep target exceeds that on the surface, close to the coils.

The disclosed method derives its effect, in part, by recognizing that in addition to considering total magnetic field strength at a given location, consideration of the strength and direction of individual X, Y, and Z magnetic vectors from an array of coils allows an arrangement of the coils to be selected such that the magnetic fields of the magnets will combine in a manner that intensifies some areas of the overall magnetic field and weakens others. In the appropriate configuration, the magnetic field along a given axis (say, for the purposes of one example, the Z-Axis defined as a radial component of energy emitted from a reference one of the coils) is augmented because when the pulsed fields from simultaneously stimulated electromagnets are combined, the field along the Z-axis is emphasized, and the net magnetic stimulation at the target at depth is greater than at superficial locations when the Z axis (radial component) of the reference magnet is directed towards the target. Such greater stimulation at depth than superficial locations avoids undesirable side effects such as seizures. This allows for the selection of a magnet array that will produce a magnetic field having an area of specific influence (i.e. one having an intensity and direction sufficient to cause a desired neurological effect) located at a select deep brain structure.

In any applicable configuration, the magnetic fields from coils in the given array are combined to generate a field having an area of specific influence at the target structure. The pulsed magnetic field over the area of specific influence induces the flow of electrical current in the target neural structure, causing the electrical potential across neural membranes to be altered. If the resultant depolarization exceeds threshold an action potential will be generated.

The principles described herein are not specific to any one coil design or composition (e.g., the coil shape or whether the coils have an iron core or not) as long as the chosen array generates a magnetic field profile that will produce an area of specific influence at the desired location. The coil array can be stationary or moved during stimulation, and additional coils can be added to the array in order to augment its function. In the appropriate applications, stimulating at depth using the Deep Brain Stimulation/Modulation techniques described herein could provide significant health benefits.

Figure 1A:
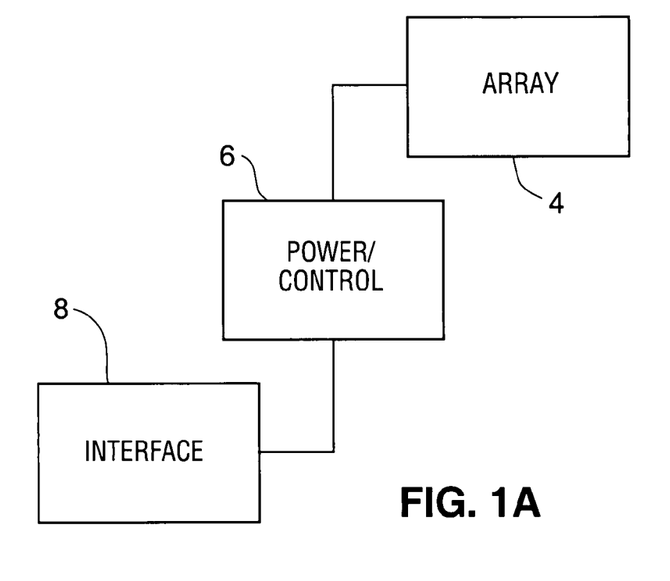
FIG. 1A is a simplified block diagram of a neuromodulation system using principles described herein.

FIG. 1A is a simplified block diagram of a neuromodulation system 2 of a type suitable for use with the methods and magnetic arrays described herein. System 2 includes a magnetic array 4, a power and control system 6, and a user interface 8 which may include one or more input devices (e.g. keyboard, mouse, touch screen, foot pedal) allowing a user to select stimulation parameters and initiate a treatment sequence.

Various power and control systems 6 may be used with the disclosed embodiments. One suitable power and control system 6 is the Magstim SuperRapid (Magstim, LTD, Wales, U.K.) power system and controller under the custom control software application running on an associated computer. Power is set in accordance with computations of the power necessary to exert the desired effect at the selected brain location.

The array 4 may be equipped with electromagnets such as the Magstim double coil (outer diameter of each coil is 70 mm) electromagnet (Part Number 9925-00), or equivalent magnets to produce the magnetic fields. Double-coils (including figure-eight and butterfly coil configurations) produce a focused magnetic field at the intersection of the two circles of the figure-eight and may be preferable for use in practicing the disclosed methods. Alternative coils may instead be used, some of which are described in connection with FIG. 5. The direction of the current for a given electromagnet can be reversed, if necessary.

Figure 1B:
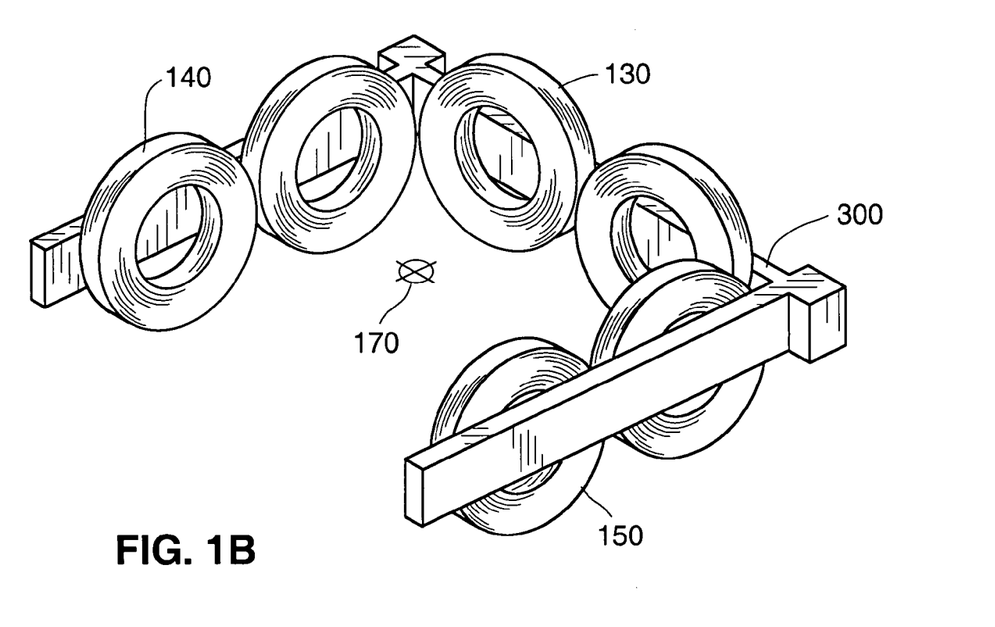
FIG. 1B shows a three-electromagnetic coil embodiment in perspective with a sample target.

A preferred magnet array includes three double-coil electromagnets at 0, 90, and 180 degrees on a circular or oval frame aimed inwards towards the designated target with additional coils possible. For example, FIG. 1B shows an embodiment with three electromagnetic coils shown in perspective. The coils 130, 140, 150 are held in a frame 300. A support (not shown) is used to maintain the frame in the desired position relative to the head of the patient. The frame 300 will generally be positioned with the coils surrounding a portion of the patient's head.

Figure 1C:
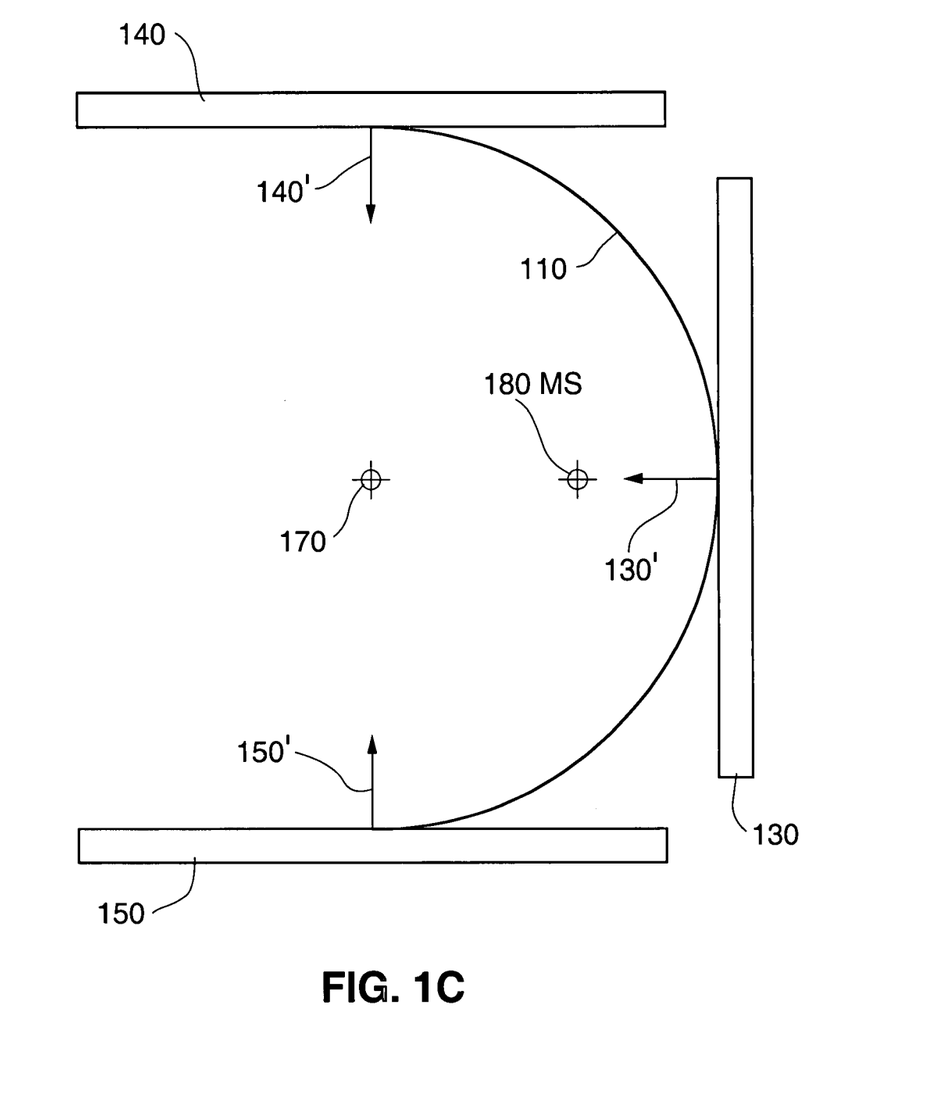
FIG. 1C shows a plan view of the configuration of the array of three magnets shown in FIG. 1A, illustrating the magnets mounted to an alternative frame.

FIG. 1C, which is a view from above, shows the electromagnets 130, 140, 150 held orthogonally in an array mounted on frame 110. In this embodiment, frame 110 is a circular or oval frame aimed inwards towards the target. Electromagnet 130, with its center aimed in radially from the 90-degree position, is a double-coil, typically 70 mm in diameter each, but is not restricted to this dimension. The frame is oriented such that the target 170 to be stimulated is located where radial components of the electromagnets intersect. Target 170 is an identified three-dimensional area of the brain of a patient whose head is disposed within the frame. In the FIGS. 1B and 1C embodiment, the radial components 130', 140', 150' selected to intersect at the target 170 correspond to the geometric centers of the electromagnetics 130, 140, 150. In other words, in this embodiment the radial component 130' of electromagnet 130 is the radial component where the two coils of the electromagnet come together and corresponds to the region where the field strength from the electromagnet 130 is highest at any given distance from the electromagnet 130 (see the field strength lines 190 shown in FIG. 2). In other embodiments, the intersecting radial component from a particular electromagnet may or may not correspond to the region of highest field strength for that magnet or the geometric center of that electromagnet.

Electromagnet 130 is termed the "reference magnet," and the radial component 130' of its magnetic field is designated as the Z axis for the purposes of this description. In FIG. 1C, this Z axis is coincident with the Z axis of the overall coordinate system in which the Z axis extends horizontally on the page, the X axis runs vertically on the page, and the Y axis is oriented perpendicular to the plane of the page. In the preferred embodiment, electromagnets 140 and 150 (which are also preferably double-coil electromagnets) have their centers aimed in radially from the 0- and 180-degree positions, i.e. such that the radial axes 130', 140', 150' of the electromagnets 130, 140, 150 are separated by 90°. In this embodiment, the target position 170 is in the plane in which the center axes of electromagnets, 130, 140, 150, are located. A representative superficial location is position 180 (also designated as MS for Middle Superficial), considering the nose of the patient pointed north to the 0-degree position).

As discussed, the system described herein arranges the magnets such that radial components from the magnets meet at deep target structures, thus allowing the system to direct a higher magnetic field at deep target structures (e.g. target 170) than at superficial positions (e.g. structure 180). According to the disclosed embodiments, ratios of Z-Axis magnetic field at the target versus superficial locations typically fall within a range of 1.5:1 to 8.5:1.

Figure 2:
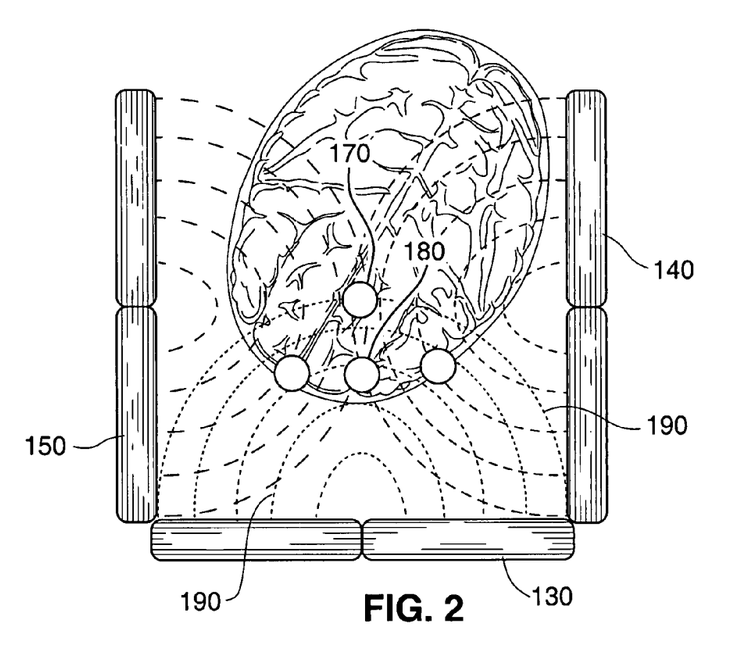
FIG. 2 shows a cross-sectional top view of a head and bran and schematically illustrates magnetic energy patterns from the coil arrangement of FIGS. 1B and 1C.

The inventors of the disclosed system believe that when magnetic energy from a TMS coil is directed into a patient's head, a substantial radial component (along with other vector components) of the energy will penetrate the skull, meninges, and their associated surface charges. This is supported by recent work by authors such as Wagner (Wagner T A, Zahn M, Grodzinsky A J, Pascual-Leone A; Three-Dimensional Head Model Simulation of Transcranial Magnetic Stimulation. IEEE Transactions on Biomedical Engineering. Vol. 51, NO. 9, September 2004. 1586-1598). Coil arrangements according to the disclosed system and method are selected such that the Z-axis magnetic field generated by the reference coil 130 makes the primary contribution needed to achieve the desired effect in the target structure. Energy emitted from the coils 140, 150 contribute to the effectiveness of the Z-axis field by shaping the field of the reference coil 130. Specifically, it is believed that the magnetic fields generated by the coils 140, 150 cancel lateral portions of the magnetic field produced by reference coil 130, allowing the radial component 130' of the reference coil's field (i.e. the portion lying along the z-axis), to be of optimal strength for stimulation. The energy emitted by coils 140, 150 also contributes to the Z axis energy; but those effects are small relative to the Z axis energy from the reference coil. Thus, as best shown in FIG. 2, energization of the coils 130, 140, 150 will produce a magnetic field concentrated at the target 170, while the coils 140, 150 will diminish the magnetic field of the reference coil at locations offset from the vector 130'.

Although the FIG. 1B embodiment shows a Z-axis component as being the primary component for stimulation, in one alternative embodiment, a magnetic field having a radial component along an axis other than the Z axis may be the one directed towards and having the most impact on the target. Moreover, although the FIG. 1B embodiment shows an array in which the radial component of coils 140, 150 are offset from the radial component of coil 130 by approximately 90°, alternative angular offsets may be used, including but not limited to angles of 45°. In another alternative embodiment, coils 130 and 140 might be separated from one other by an angle that differs from the angle separating coils 130 and 150.

Figure 3:
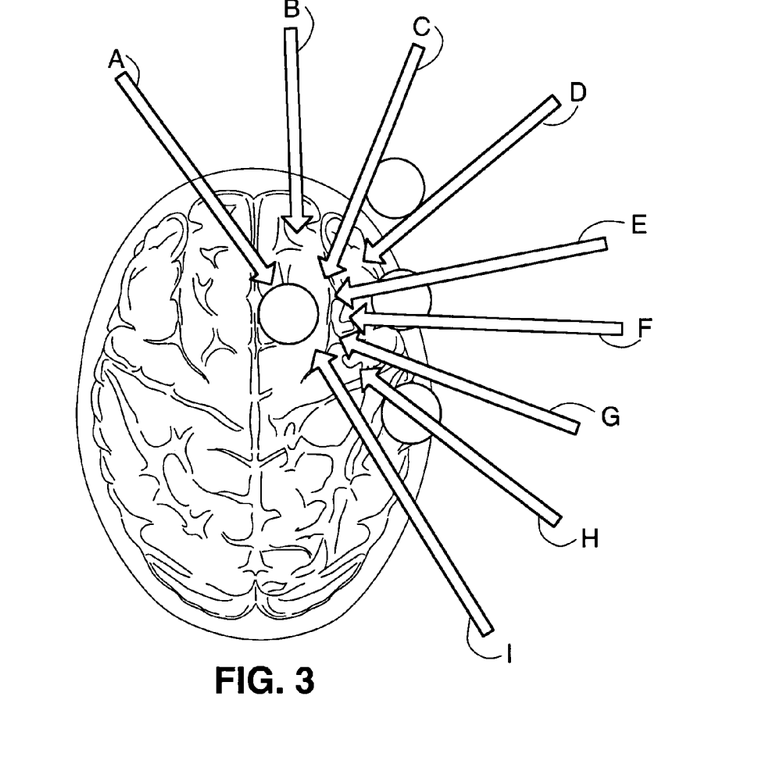
FIG. 3 shows a cross-sectional top view of a head and brain and schematically illustrates a number of radial components of magnetic fields emitted from hypothetical magnetic coils positioned at a variety of locations.

Thus, referring to FIG. 3, while a preferred combination of coils might include radial components along axes designated A, E and I, other suitable combinations of magnets might be employed having radial components along other combinations of the axes, including select ones of the illustrated axes A through I. In any case, it is most desirable to select magnet arrays that will generate higher electric fields at the target than at superficial structures. More arbitrary positioning of electromagnets can inhibit the desired enhancing of the field at the target depth. For example, while an array of coils producing radial components along axes A, E and I in FIG. 3 might give beneficial results, stimulating with radial components along axes A, E and I in combination with radial components along other ones of the illustrated axes can produce a Z-axis field strength that is significantly lower than that produced when only the A, E and I axis coils are energized.

In another alternative embodiment, the electromagnets in the array are oriented and pulsed such that the magnetic-field vector with the greatest impact is one comprised of magnetic fields emitted by coils oriented with their radial components positioned along a suitable combination of axes. In other words, the vector having the greatest impact need not necessarily coincide with a radial component of one of the electromagnets but may be transverse to the radial components of all of the electromagnets.

The FIG. 1B array uses an array of three electromagnetics, whereas in other embodiments additional electromagnets might be added at suitable angles selected to produce depolarization at the target deep tissue sight. Such embodiments may include configurations where the electromagnets are not placed at equal angles of separation. The selected combination of radial components may or may not lie within a single plane.

Figure 4:
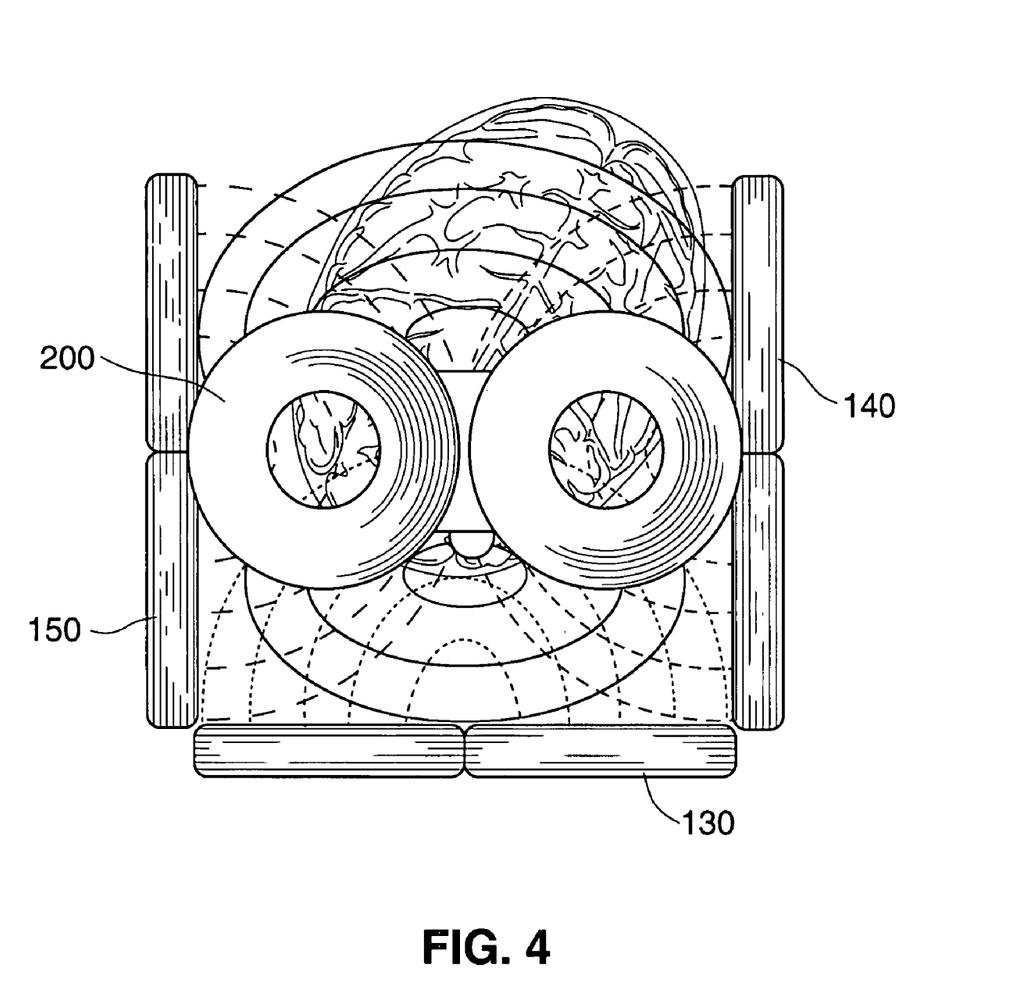
FIG. 4 shows a plan view of an alternative array using four magnets.

For example, referring to FIG. 4, a coil array as shown in FIG. 1 may be supplemented by a fourth coil 200 facing in toward the intersection of those three coils 130, 140, 150 having radial components on the same plane. In such a case, the radial component of the magnetic field from the fourth coil intensifies the strength of the magnetic field where the vectors from the coils 130, 140, 150 converge. The coil 200 is energized either simultaneously with the other coils or it is energized sequential with energization of the coils 130, 140, 150 such that the field vectors combine with that of the other coils in the manner desired. In such an embodiment, the three coils 130, 140, 150 in the single plane might be oriented along the sides of a patient's head, while the fourth coil 200 might be on top of patient's head, pointing downward.

Although the figures show arrays in which electromagnets are of the same type, the electromagnets in the array need not be the same type. For example, the coils 130, 140 of FIG. 1B might differ in size, or one might be a figure-eight type of coil and the other might be a butterfly coil. Moreover, in any of the described embodiments, the absolute size and/or number of electromagnets is selected such that the size of the electromagnets relative to the distance to the target and the orientation of the electromagnets included in the array are such that the resulting effect at the target depth is augmented rather than diminished.

The array is preferably positioned relative to the target so as to achieve optimal access to the target and so as to aim energy towards the target in a manner that avoids delivery of large overall or vector component field strengths to structures that are not to be stimulated target structures. Accordingly, while the internal angular relationships (e.g. in the FIG. 1B example the 0-, 90-, and 180-degree positions of the electromagnets 130, 140, 150) are preferably fixed with respect to one another, the array itself may be placed in a variety of positions so as to meet the needs of the particular application. During use the array is thus positioned such that current will be induced in the neural structure of interest so action potentials will be fired to get the desired immediate effect, short-term effect, or long-term training effect. For example, referring again to FIG. 1C, to direct the enhanced vector 130' to an off-center target, one can position the coil array off-center with respect to the head and/or tilt it at a suitable angle to appropriately stimulate the target. In addition, there may be other local maxima and minima of the magnetic field that can be usefully employed.

In some alternative embodiments, more than one anatomical location may be simultaneously targeted. An example of this would include the situation in which one location is the primary target and one or more other locations are connected neural pathways which can have a secondary effect upon the primary target. If the secondary target causes a reaction which indirectly augments the intended effect upon the primary target, the intended neuromodulation effect is thereby enhanced.

The three-dimensional position of the target may be determined using known methods, such as by mapping coordinates from imaging and brain atlases as well as functional MRI and demonstrated activation with the TMS. Such methods are known and used in the art in connection with TMS and radio-surgical procedures. The positioning of the array relative to the patient need not be carried out manually. For example, one can use robotic position devices as discussed by Fox et al. in U.S. Patent Applications 20050113630 and 20030050527.

Examples of conditions that may be treated with the disclosed system, as well as brain structures that may be targeted for treating those conditions, include:

Parkinson's Disease: subthalamic Nucleus, globus pallidus extema

Depression: Anterior cingulate gyrus, posterior cingulate gyrus, subgeniculate cingulate gyrus.

Chronic Pain: Anterior cingulate, dorsal cingulate gyrus, motor cortex

Obesity: Ventromedial nucleus of thalamus, Ventrolateral nucleus of thalamus

Figure 5:
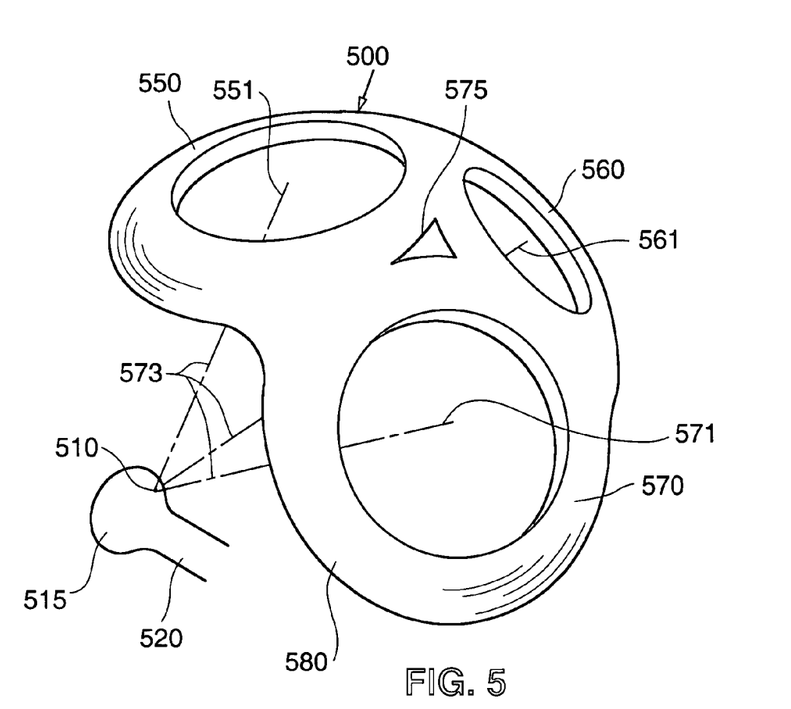
FIG. 5 is a perspective view of yet another alternative magnet array.

Obsessive Compulsive Disorder: Anterior limb of the internal.capsule, subthalamic nuclei Addiction: Nucleus: accumbens, septum Alzheimer's Disease: hippocampus, posterior cingulate gyrus In an alternative embodiment shown in FIG. 5, coil array 500 is comprised of coils 550, 560, and 570. Each coil includes concentric loops of insulated conductive material (580). In this example each of these coils is of approximately equal size and shape, and the difference in their appearance in the figure is due to the perspective view. Importantly, this coil array represents an optimized compromise between four design parameters that frequently conflict with one another:

(a) First, coils 550, 560, and 570, within array 500, are each oriented so that the normal (radial) component (551,561, 571) of the energy that they deliver points toward a single common convergence point 510, located at a substantial distance below array 500. Convergence point 510 has a predetermined spatial relationship to the intended target. In the embodiment shown wherein the array is composed of single rather than double coils, the convergence point will have a lower level of total energy than will areas lateral to the convergence point. Hence, placing the convergence point lateral to the intended target may be preferable, depending upon the desired effect and the specific nature of the surrounding anatomy. The target may be an axonal structure 520 or a grey matter structure 515 alone, without proximity to the other, or it may be at the junction of the two;

(b) Second, conformality of the array to the surface of the body (e.g. head) over which it is applied, minimizes energy loss within space outside the body;

(c) Third, maximization of the radius dimensions of each coil loop maximizes magnetic field power delivery;

(d) And finally, minimization of the coil array 500 overall size, so as to be able to position the array 500 on the body (e.g. head) of a patient minimizes the chance of stimulating sensitive non-target structures, even as the intended target is stimulated.

In order to accomplish this optimization, compromises made include minimizing the size of intracoil space 575, and a distortion of the shape of coils 550, 560 and 570 from pure circular forms into a shape in which the component loops have a somewhat triangular configuration. In such an embodiment, local minima and maxima in magnetic field strength are achieved in terms of specific vector components of the total field, as was demonstrated with the 90 degree array embodiment of FIG. 1B.

For each embodiment, stimulation parameters (e.g. pulse rate, pulse width and power) are determined based on the stimulation dose needed at the target. Stimulation dose may be derived as a predetermined percentage of the patient's resting motor threshold as determined (using known techniques) by delivering stimulation pulses over a determined region of the motor cortex and determining the power level at which visible movement of the corresponding part of the body (e.g. the right thumb) occurs. Typically the stimulation dose is in the range of 100-120% of the measured motor threshold for reaching a superficial cortical structure. To reach a deeper structure, a dose that is higher relative to the motor threshold is used to compensate for the fall-off of the energy field as it moves away from the source. The selected dose may also take into account the energy distribution produced by the array, and the pulse rate and duration. If stimulation is undesired, a dose below the stimulation threshold will be used. The individual vector components at points more superficial than the target at depth will be preferably maintained below the motor threshold.

In some cases, the stimulating magnetic field at the target is augmented by additional input stimulation coming from neural pathways that themselves are being stimulated by superficial neural-tissue stations that have been triggered by superficial magnetic-field stimulation.

In the selected array, all coils need not be driven with the same amount of power or direction of current, as long as the combined magnetic field is appropriate for the target depth and desired effect. Similarly, the pattern and/or frequency of pulses may also not necessarily be the same for each electromagnet in the configuration.

The system may employ a pulse pattern that is constant over the treatment duration or one in which the pattern of the magnetic-field pulses is interrupted at various points and intervals of time. This latter approach, for example, might be useful for protecting sensitive neural structures placed in the stimulation path between an electromagnet coil and the target.

A likely target position will be at the bend of an axon bundle (Ruohonen, 1998). The total magnetic field is not the most pertinent measure of predicted effect, because the directionality is critical to the induction of electrical current and thus the triggering of neural action potentials. Power levels to the magnets are set to a level that will obtain the desired effect without overwhelming superficial structures with resultant side effects such as a seizure. A software model for accomplishing this has been developed and is described herein.

Magnetic fields affect neurons by virtue of their ability to transform into an electric field within the aqueous medial surrounding neurons, and within the neural membranes themselves. The propensity for a magnetic field to transform into an electric field is controlled by factors such as the electrical conductivity of the media, and the local geometry within the anatomy. For this reason, the point of peak electric field within a human head may be spatially displaced from the point of maximal magnetic field. Consequently, it is a further object of the disclosed systems to provide a method by which the aim of a neuromodulation device such as that described herein may be offset, compensated for, re-aimed, or re-calibrated, so as to compensate for predicted or observed magnetic/electric field maxima displacement. For example, if the target structure lies within a region of lower conductivity than a non-target region immediately next to it, at least three offset strategies may be employed.

According to a first off-set strategy, the calculated magnetic field is moved so as to minimize the field strength at the highly conductive non-target, and to better maximize it at the less conductive target region. This may be accomplished in several ways, including (a) physical movement of the entire coil array, for example with a robot; and/or (b) changing the relative power between the various coils in the array so as to shift the field profile.

In a second off-set strategy, the calculated magnetic field is moved using the methods described in the previous paragraph so as to displace the "target" to a region of high conductivity that connects to the original target.

In a third exemplary off-set strategy, the overall power output of the coils is changed so as to increase the electric field at the target sufficiently, keeping in mind that the greater electric field at the non-target site will also be increased.

MRI imaging, for example, diffusion tensor imaging methods, may be particularly useful for inferring conductivity as well as geometry of biological tissue. In this manner the "highways" of high conductivity—basically the aqueous media surrounding nerve bundles—may be identified such that electric field within these highly conductive regions may be efficiently transferred to targeted regions of lesser conductivity. This process may be compared with pins on an IC chip receiving signals via current remotely applied to traces on a printed circuit board. Models of electric field generation have been developed, for example, by Wagner (Wagner, et al. 2004), which predict the amount propensity of tissue at given locations to generate and propagate electric field and can be used as the basis for such offset calculations.

Accordingly, a target planning system 600 (FIG. 6) including a graphical user interface can be utilized in the treatment-planning phase to flag magnetic/electric field displacements, as they bear upon designated targets, and non-targeted critical structures. Such an interface may contain a tool with which to correct for this displacement, in consideration of projected consequences of that displacement. In one embodiment such treatment-planning system and software represented schematically in FIG. 6 includes means to coordinate two, three or more spatially representative data sets: (a) one data set 602 representing the calculated magnetic field strength distribution generated by the array, (b) another data set 604 representing the pertinent anatomy, including the target (for example, a 3-dimensional standard structural or a "functional" image such as PET or fMRI which shows the metabolic activity of various regions). Another exemplar (c) (labeled 606) represents the propensity of the target to convert magnetic field into electric field. This data set may be derived, for example, from a diffusion tensor MR image, or from maps obtained constructed from a composite of sources (e.g., Wagner, et al 2004). In some cases, data sets (b) and (c) can be effectively represented by a single data set, such as a diffusion tensor MR image.

Figure 6:
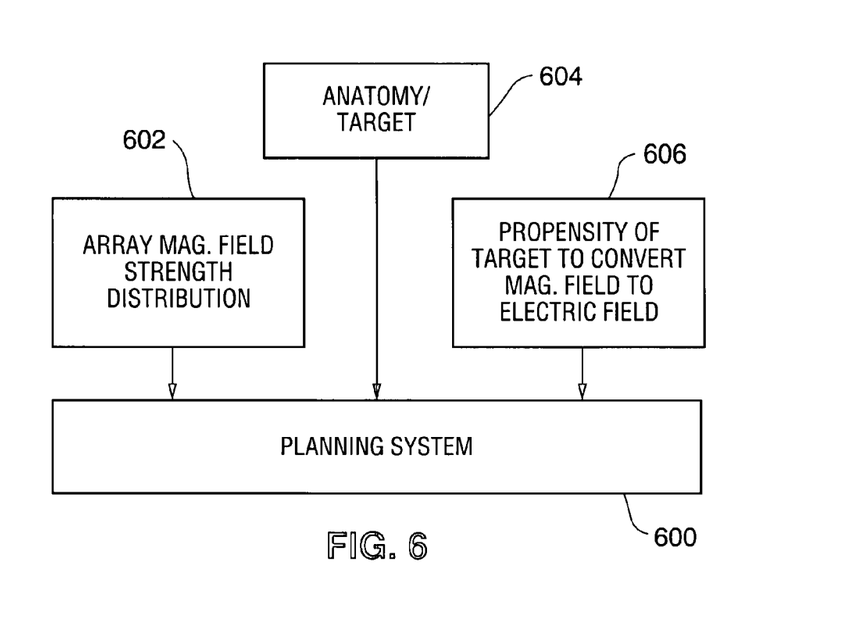
FIG. 6 schematically illustrates a planning system useful for determining stimulation parameters.

By registering the data sets 602, 604, 606 onto a single coordinate system visual representations of the data sets may be displayed using the graphical output. Methods for moving two or more spatially representative data sets with respect to one another are known in the art, and include approaches described in U.S. Pat. No. 5,531,227 (Schneider 1996), U.S. Pat. No. 6,351,573 (Schneider 2002), U.S. Pat. No. 5,891,034 (Bucholz 1999), and U.S. Pat. No. 6,236,875 (Bucholz 2001). The user can use the output of the planning system to predict displacement of the energy field and can select an array position, overall power, and/or relative power levels amongst the coils to ensure stimulation at the desired dose is achieved at the intended target. Alternatively, the planning system might process the data sets to identify the needed stimulation parameters (such as array position, power output, relative power of each coil, pulse frequency and duration) and to control some or all of the stimulating parameters (e.g. by controlling motors associated with a robotic positioning system for the array, and/or by controlling the output parameters of the stimulation pulse). Planning system 600 may be part of the power and control system 6 (FIG. 1A), or it may be a separate system.

In some applications it may be advantageous to move the array during the course of treatment. One example is to reposition the array over the head of the person or animal, including tilting for best access to the target. The pattern of magnetic pulses might be temporarily interrupted for repositioning (as described in the proceeding paragraph) so as to protect areas of the anatomy against unintended simulation. In other example, the array may be moved about the head of the subject during stimulation, either rotating completely around the subject or moving it over a selected 3D region. One reason for moving the array is to cause even more electrical change at the target neural membrane. Another way to accomplish this is to rapidly oscillate the electromagnets back and forth (e.g., a few degrees each way) on the axis that is perpendicular to their radial axes. Another is to alternately displace the site of maximal stimulation, thus in effect having two different pulse rates seen by the tissue, one at the target and the other at various superficial locations.

Figure 7A:
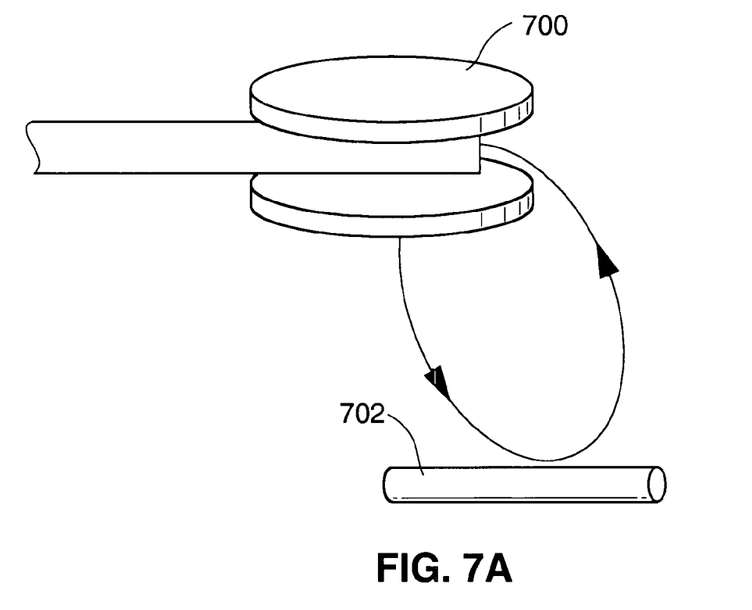
FIGS. 7A and 7B schematically illustrate two examples of movement patterns for moving a coil towards an axon bundle.
Figure 7B:
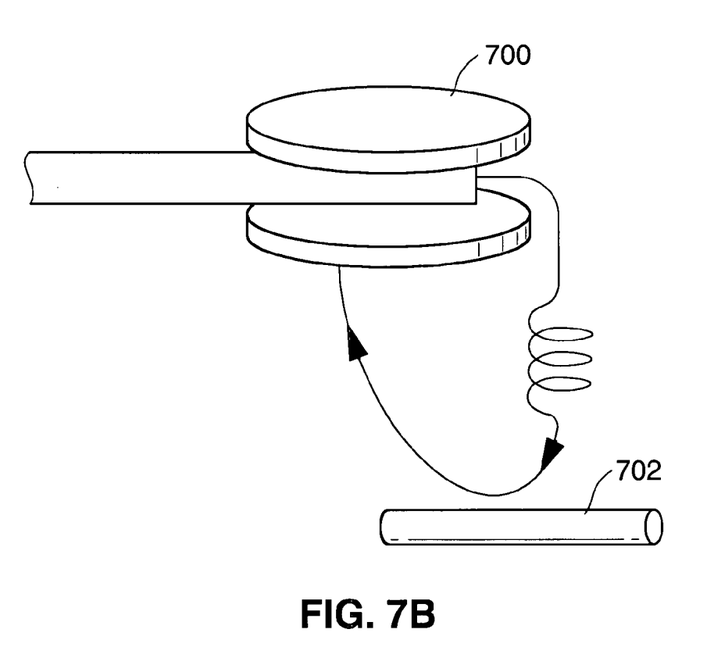

In one embodiment, the path of motion of the coil array related to a target will not be only at an angle relative to an axon bundle, but will preferably be longitudinal as well. This result in an effect akin to "milking" down (or up) the longitudinal axis of that bundle as schematically illustrated in FIG. 7A, in which 700 represents a coil and 702 represents an axon bundle. The axon bundle need not necessarily be straight, but may be curved instead. If curved, the curve may not necessarily reside in a single plane. When using a milking-tipe motion relative to the axon bundle, the motion for the "milking" component of the coil path may consist of a swooping motion that is boring in on the target along a helical path as illustrated in FIG. 7B.

In an alternative embodiment, an array of small electromagnets is used. A higher level of power may be used if the coils are equipped with a cooling mechanism (e.g., liquid nitrogen contained in a reservoir behind the electromagnets). This configuration is more useful in animals that have smaller head sizes because as noted previously, at short distances relative to the size of the electromagnet the magnetic-field profile is determined by the size characteristics or the electromagnet itself. At long relative distances, the magnetic field falls off at a ratio of one over the cube of the distance.

An embodiment that can be used with any number or size of electromagnets is one in which the electromagnets are configured in an appropriately sized helmet having suitable coiling mechanisms for the coils.

While various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents.

Any and all patents, patent applications and printed publications referred to above are incorporated by reference.

What is claimed is:

1. A method for generating higher magnetic-field stimulation at a deep brain target than at more superficial cortical non-target brain regions, the method comprising the steps of:
    selecting a deep brain target,
    positioning an array of electromagnets about a patient's head,
    orienting the electromagnets so that components of magnetic-field energy from at least two of the electromagnets intersect at the deep brain target, wherein the deep brain target is deeper in the brain and further from the electromagnets than the more superficial cortical non-target brain regions; and
    simultaneously energizing at least two of the electromagnets, whereby a stimulating vector component of the magnetic field received at the deep brain target produces stimulation at the deep-brain target which is greater than that produced at the more superficial cortical brain locations between the deep brain target and the electromagnets.

2. The method of claim 1, wherein the orienting step includes orienting the electromagnets such that, during the energizing step, radial components of energy emitted by at least three of the energized electromagnets intersect at the target.

3. The method of claim 1, wherein the energizing step includes the step of energizing at least two of the electromagnets using different magnitudes of power.

4. The method of claim 1, wherein the energizing step includes the step of energizing at least two of the electromagnets using current of opposite polarity.

5. The method of claim 1, in which the stimulating vector component is comprised of energy emitted from a plurality of the electromagnets.

6. The method of claim 1, further including the step of moving the array during the energizing step.

7. The method of claim 1, further including the step of, during the energizing step, automatically moving the array along multiple axes.

8. The method of claim 1, including the step of moving at least one of the electromagnets longitudinally and angularly relative to a target structure.

9. The method of claim 1, further including the step of reciprocating the electromagnets along an axis perpendicular to a radial component of the magnetic field of one of the electromagnets.

10. The method of claim 1, wherein the energizing step includes energizing the electromagnets according to a pulse pattern, and wherein the method further includes interrupting the pulse pattern and then resuming the pulse pattern after an interval of time.

11. The method of claim 1, in which the orienting step positions at least two electromagnets within a plane, and at least one electromagnet outside the plane.

12. The method of claim 1, where the magnetic field further causes stimulation of neural tissue, said stimulation of neural tissue generating electrical signals, and wherein the effect of the stimulating vector component on the target is augmented by the electrical signals.

13. The method in claim 1, wherein each electromagnet produces energy having a radial component, and wherein the orienting step includes orienting at least two of electromagnets such that the radial component from a first one of the two electromagnets occupies a first plane and the radial component from a second one of the two electromagnets occupies a second plane that is different from the first plane.

14. The method of claim 13, in which the first and second planes are at arbitrary angles relative to one another.

15. The method in claim 1, where the target is determined using imaging of the brain.

16. The method of claim 15, wherein the imaging step is carried out using functional MRI.

17. The method in claim 1, wherein the energizing step includes energizing a first one of the electromagnets at a first pulse frequency and energizing a second one of the electromagnets at a second, different pulse frequency.

18. The method in claim 1, wherein the energizing step includes energizing a first one of the electromagnets at a first pulse pattern and energizing a second one of the electromagnets at a second, different pulse pattern.

19. The method in claim 1, wherein the method further includes the steps of selecting a second target, and wherein the energizing step results in stimulation at the second target.

20. The method in claim 1, where the energizing step causes the electromagnets to emit patterns of pulses.

21. The method of claim 1, wherein stimulation of the target treats a condition in the patient, the condition selected from the group of conditions consisting of depression, chronic pain, Alzheimer's Disease, obsessive compulsive disorder, addictions, obesity, and Parkinson's Disease.

22. The method of claim 1, wherein the step of positioning an array of electromagnets about a patient's head comprises positioning the electromagnets around the subject's head in a non-overlapping arrangement so that none of the electromagnets is interposed between another electromagnet and the patient's head.

23. The method of claim 1, wherein positioning an array of electromagnets about a patient's head comprises positioning an array of transcranial magnetic coil electromagnets about a patient's head.

24. The method of claim 1, wherein selecting a deep brain target comprises selecting a deep brain region from the group consisting of: subthalamic nucleus, globus pallidus extema, anterior cingulate gyrus, posterior cingulate gyms, subgenual cingulate gyrus, anterior cingulate, dorsal cingulate gyrus, ventromedial nucleus of thalamus, ventrolateral nucleus of thalamus, anterior limb of the internal capsule, nucleus accumbens, septal nucleus, and hippocampus.

25. A method for generating higher magnetic-field stimulation at a deep brain target than at more superficial cortical non-target brain regions, the method comprising the steps of:
    selecting a deep brain target;
    positioning an array of electromagnets about a patient's head;
    orienting the electromagnets to deliver components of magnetic-field energy from at least two of the electromagnets to the deep brain target wherein the deep brain target is deeper in the brain and further from the electromagnets than the more superficial cortical non-target brain regions; and
    energizing at least two of the electromagnets, whereby the combined magnetic-field energy emitted from the at least two electromagnets stimulates the deep brain target more that it stimulates the non-target brain regions located between the deep brain target and the electromagnets.

26. The method of claim 25, wherein selecting a deep brain target comprises selecting a deep brain region from the group consisting of: subthalamic nucleus, globus pallidus extema, anterior cingulate gyrus, posterior cingulate gyrus, subgenual cingulate gyrus, anterior cingulate, dorsal cingulate gyrus, ventromedial nucleus of thalamus, ventrolateral nucleus of thalamus, anterior limb of the internal capsule, nucleus accumbens, septal nucleus, and hippocampus.

27. A method for generating higher magnetic-field stimulation at a deep brain target than at more superficial cortical non-target brain regions, the method comprising the steps of:
    selecting a deep brain target;
    positioning an array of electromagnets about a patient's head;
    orienting the electromagnets so that components of magnetic-field energy from at least two of the electromagnets intersect at the deep brain target to deliver magnetic-field energy components to the deep brain target wherein the deep brain target is deeper in the brain and further from the electromagnets than the more superficial cortical non-target brain regions; and
    simultaneously energizing at least two of the electromagnets, whereby a stimulation from the electromagnets that is received at the deep brain target is greater than that received at the more superficial non-target brain regions located between the deep brain target and the electromagnets.

28. The method of claim 27, wherein selecting a deep brain target comprises selecting a deep brain region from the group consisting of: subthalamic nucleus, globus pallidus extema, anterior cingulate gyrus, posterior cingulate gyrus, subgenual cingulate gyrus, anterior cingulate, dorsal cingulate gyrus, ventromedial nucleus of thalamus, ventrolateral nucleus of thalamus, anterior limb of the internal capsule, nucleus accumbens, septal nucleus, and hippocampus.

29. A method for generating magnetic-field stimulation more intensely at a deep brain target than at more superficial non-target regions of the brain, the method comprising the steps of:
    positioning an array of electromagnets about a patient's head;
    orienting the electromagnets so that components of magnetic-field energy from at least two of the electromagnets intersect at the deep brain target to deliver magnetic-field energy to a deep brain target wherein the deep brain target is deeper in the brain and further from the electromagnets than the more superficial non-target brain regions; and
    simultaneously energizing at least two of the electromagnets from different positions about the patient's head to stimulate the deep brain target with a magnetic field at the target that is greater than the magnetic field received at the non-target brain regions located more superficially, between the deep brain target and the electromagnets.

30. A method for generating higher stimulation at a deep brain target within the brain than at more superficial cortical non-target brain regions, the method comprising the steps of:
    selecting a deep brain target;
    positioning an array of electromagnets about a patient's head in a non-overlapping arrangement so that none of the electromagnets is interposed between another electromagnet and the patient's head, wherein the array of electromagnets is oriented so that components of magnetic-field energy from at least two of the electromagnets intersect at the deep brain target to deliver magnetic-field energy to the deep brain target; and
    simultaneously energizing at least two of the electromagnets to emit magnetic energy, whereby the energy received at the deep brain target produces stimulation at the deep-brain target which is greater than that produced at the more superficial cortical non-target brain locations between the deep brain target and the electromagnets.

31. The method of claim 30, wherein selecting a deep brain target comprises selecting a deep brain region from the group consisting of: subthalamic nucleus, globus pallidus extema, anterior cingulate gyrus, posterior cingulate gyrus, subgenual cingulate gyms, anterior cingulate, dorsal cingulate gyms, ventromedial nucleus of thalamus, ventrolateral nucleus of thalamus, anterior limb of the internal capsule, nucleus accumbens, septal nucleus, and hippocampus.

* * * * *